United States Patent [19]
Lawes et al.

[11] Patent Number: 5,258,033
[45] Date of Patent: Nov. 2, 1993

[54] TOTAL HIP REPLACEMENT FEMORAL COMPONENT

[75] Inventors: Peter Lawes, Maidenhead; Robin S. M. Ling, Exeter, both of England

[73] Assignee: Howmedica International Inc., Shannon, Ireland

[21] Appl. No.: 736,151

[22] Filed: Jul. 26, 1991

[30] Foreign Application Priority Data

Aug. 8, 1990 [GB] United Kingdom ............... 9017402

[51] Int. Cl.⁵ ..................... A61F 2/36; A61F 2/30
[52] U.S. Cl. ........................... 623/23; 623/22; 623/18
[58] Field of Search ................... 623/16, 18, 22, 23

[56] References Cited

U.S. PATENT DOCUMENTS

| | | | |
|---|---|---|---|
| 4,005,495 | 2/1977 | Locke et al. | 623/18 |
| 4,123,806 | 11/1978 | Amstutz et al. | 623/22 |
| 4,332,036 | 6/1982 | Sutter et al. | 623/18 |
| 4,846,841 | 7/1989 | Oh | 623/23 |

FOREIGN PATENT DOCUMENTS

| | | | |
|---|---|---|---|
| 2304324 | 10/1976 | France | 623/23 |
| 2361861 | 3/1978 | France | 623/23 |

*Primary Examiner*—David Isabella
*Attorney, Agent, or Firm*—Peter C. Richardson; Lawrence C. Akers; Raymond W. Augustin

[57] ABSTRACT

A total hip replacement femoral component has an outer surface shaped to conform to an acetabular socket and has an internal bore adapted to receive a femoral head. The head has been shaped and dimensioned to provide a spigot to enter the bore and be locked in place by a cement mantle between the bone and the walls of the bore. The head allows the hip component to move further over said spigot and re-lock should the cement creep or thereby any movement in the bone after assembly. The internal bore is inwardly tapered. Thus the taper can be co-axial with the femoral neck, but there may be advantages in orientating the axis of the taper as close to vertical as possible when in position so that it is closer to the average force vector acting on the femoral head during human activity.

10 Claims, 3 Drawing Sheets

TOTAL HIP REPLACEMENT FEMORAL COMPONENT

BACKGROUND OF THE INVENTION

This invention relates to a total hip replacement femoral component.

Total hip replacements conventionally use a long intramedullary stem passing the marrow cavity of the bone. These are very successful but when they fail the long stem can create considerable damage inside the bone. It can cause a fracture through the bone around the level of the tip of the stem. The implant can wobble about inside the bone causing the intramedullary cavity to become larger and larger. Revision of failures is always difficult for a surgeon.

Surgeons have always called for a more conservative device. The Smith-Peterson cups of the 1920's and 1930's were merely free floating substantially hemispherical shells placed between the top of the femur and the acetabulum. Apart from paring away the cartilage, there was no bone removal. They were not very successful and the constant movement of bone against metal as the joint moved eventually caused severe bony erosion. In the mid-1940's Judet in France designed a prosthesis whereby the majority of the femoral head was removed and a replacement device was fitted with a peg or nail which passed a short way down the femoral neck. These lasted a little longer than the Smith-Peterson cups, but not much. Small movement of the device against the bone caused friction of the bone and the bending loads on the peg often caused them to break out underneath the bony femoral neck. In the mid-1970's, double cup arthroplasty was tried. There were several designs: Wagner in Germany, an Italian Group, Imperial College and London Hospital (ICLH) and the Tharies design from Amstutz in California. These all removed a fair proportion of the femoral bearing surface by turning it down to a cylindrical form or hemispherical form. A metal shell was then fixed with bone cement on the remaining bony peg. The acetabular cup was quite conventional. Unlike normal total hips, however, which have standard femoral head sizes of 22 mm, 26 mm, 28 mm and 32 mm, these double cup arthroplasties have to have large bearing surface diameters closer to the original hip, typically 40 mm or 41 mm for a small size, 45 mm or 46 mm for a medium size and 50 mm or 51 mm for a large size. These latter double cup designs commonly failed either by a crack progressing around the bone cement between the prosthetic femoral shell and the bone or by a fracture of the bone across from one side of the prosthetic femoral component rim to the other.

SUMMARY OF THE INVENTION

It is an object of the present invention to provide a more successful surface replacement of the femoral side of a total hip because the absence of the stem is undoubtedly more conservative and is preferred over the stemmed variety by a great many surgeons.

According to the present invention, a total hip replacement femoral component has an outer part spherical surface shaped to conform to an acetabular socket. The femoral component has an internal bore adapted to receive a femoral head which has been shaped and dimensioned to provide a spigot or trunion. The bore receives the head and is locked in place by a cement mantle and includes a spacer which creates a void to allow the component to move further over the spigot and re-lock should the cement creep or because of any movement in the bone after assembly. The bone can be prepared to provide a cylindrical or slightly tapering spigot or trunion.

In the preferred embodiment the internal bore of the femoral component is inwardly tapered. Thus, the taper can be co-axial with the femoral neck although there may be advantages in orientating the axis of the taper slightly more vertical when in position so that it is closer to the average force vector acting on the femoral head during human activity.

With this tapered bore the interface between the bone cement and the bone is protected against shear and damage, and any movement preferably takes place between the bone cement and the prosthesis. The bore may be arranged to be slightly oval or it can be multi-faceted or it can be provided with grooves and/or ridges which extend longitudinally thereof to prevent rotation relative to the spigot. The bore may conveniently have a polished surface to ensure that any movement which takes place is preferably between the bone cement or the outer surface of the spacer and the prosthesis and not between the bone cement and the bone itself.

The spacer is included for preventing cement from reaching the bottom of the bore. The spacer causes a void into which the spigot can move after assembly if the cement creeps or if there is any movement in the bore. This spacer may comprise a cap which is dimensioned to fit in the bore towards the blind end thereof and the distally facing external side of which is engaged by the proximal end of the spigot when located therein. The cap can be a flat disc or it can be cup-shaped having side walls within which the spigot is located when in position.

In another preferred embodiment the walls of the cup-shaped spacer extend outwardly to cover all the internal wall of the bore surrounding the spigot when in position. The spacer can be pre-fitted either by the manufacturer or by the surgeon inside the bore of the femoral component and is preferably made of a material similar to bone cement, for example, polymethylmethacrylate, to make it fully compatible with the bone cement. The void which is left in the blind end of the bore can be typically 3 mm or 4 mm inside the femoral component. With this arrangement the bone cement can be applied to the bone or to the prosthetic femoral head immediately before the implant is fitted.

In another arrangement, the spacer can be in the form of a collar which fits over the spigot and extends towards its distal end. With this arrangement, however, a surgeon must be careful to apply the cement around the exposed portion of bore, not over the void creating spacer. The spacer acts to allow the spigot to sink further into the bore without its proximal end reaching the inner blind end of the bore and thus preventing this internal movement.

The bore may conveniently have a polished surface to ensure that any movement which takes place is preferably between the bone cement or the outer surface of the spacer and the prosthesis and not between the bone cement and the bone itself. Any rotation preventing feature, such as bore ovality or multi-facets or grooves must extend lengthwise, or substantially lengthwise, and may include slight spiralling. No circumferential grooves or ridges can be permitted which will resist re-engagement of the tapered spigot with the taper bore.

BRIEF DESCRIPTION OF THE DRAWINGS

In the drawings wherein similar reference characters denote similar elements throughout the two views.

DESCRIPTION OF THE PREFERRED EMBODIMENT

Figure 1:
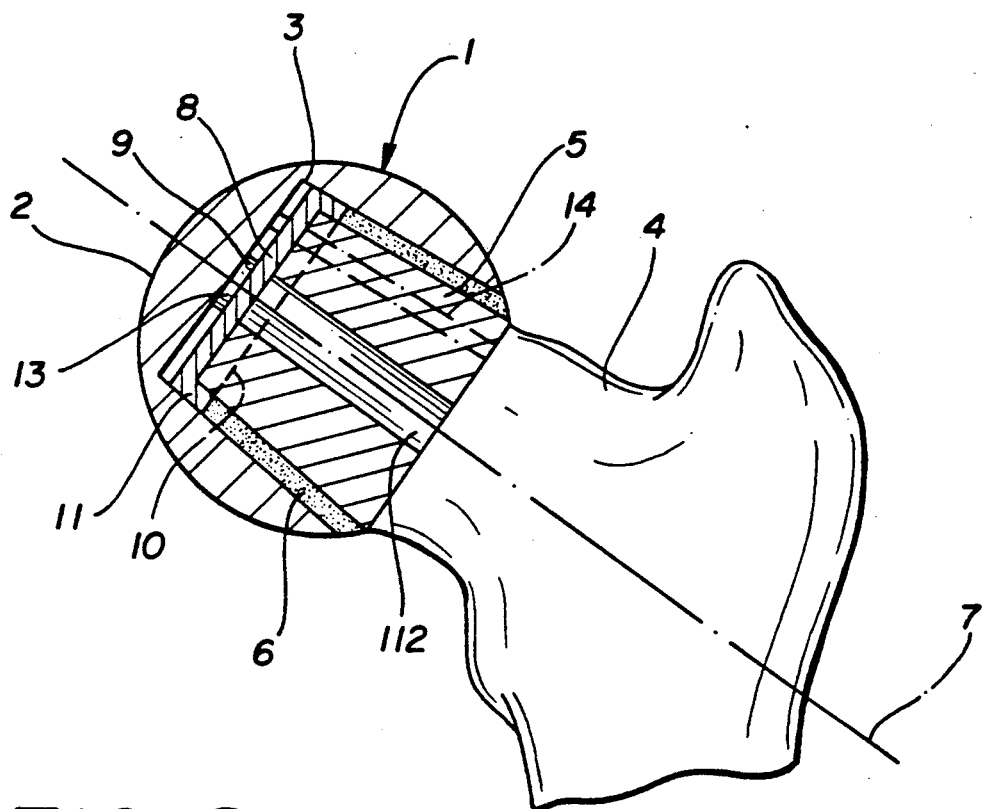
FIG. 1 is a diagrammatic cross-section through a femur provided with the femoral component according to the invention.

As shown in FIG. 1, the total hip replacement femoral component indicated by reference numeral 1 has an outer surface 2 in the usual ball shape to conform to an acetabular socket. An internal bore 3 is provided which is inwardly tapered at an angle of about 1° to 20° and in the preferred embodiment shown is substantially circular. The component is made from a stainless steel, for example, and the internal surface of the bore 3 is highly polished. If desired, the taper could be parabolic or a truncated parabola.

The femoral head 4 on which femoral component 1 is to be used is shaped and dimensioned to provide a substantially circular tapered spigot or trunion 5. The angle of the taper is similar to the angle of taper of the bore 3 and is dimensioned so that it will lock into position when held in place by cement 6. The preferred taper of spigot 5 is co-axial with the femoral neck, the general axis of which is indicated by the broken line 7. There may, however, be an advantage in orientating the axis of the taper closer to the vertical so that it is closer to the average force vector acting on the femoral head during human activity.

A spacer 8 is provided which is shaped and dimensioned to fit closely within bore 3 towards its inner or blind end but leaving a space 9 which may be typically 3 mm or 4 mm deep. It will be seen that spacer 8 is provided as a cup-shaped cap for covering the proximal end of the spigot and is dimensioned so that the side walls 11 of the cup locate on the proximal end 10 of the spigot when spacer 8 is in position. Spacer 8 can be pre-fitted into bore 3 either by the manufacturer or the surgeon prior to use and is made from polymethylmethacrylate so that it is fully compatible with the bone cement which will be of the same material. If desired, the spacer could be provided as a substantially flat disc.

Figure 2:
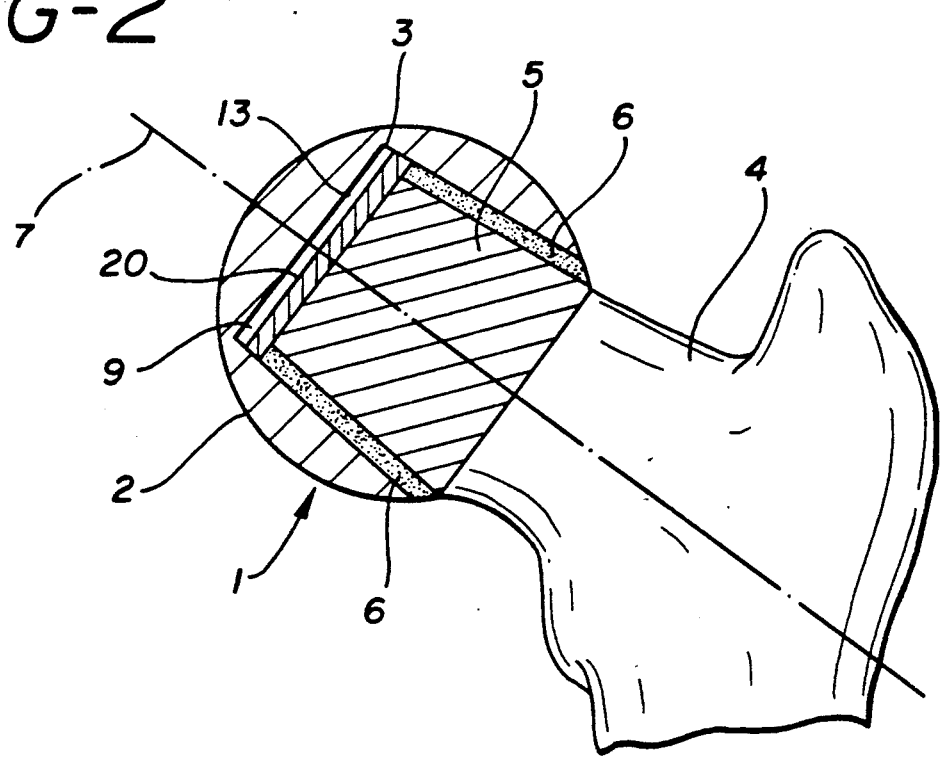
FIG. 2 is a similar view of an alternative embodiment of the present invention.

If desired, the void creator could be provided as a substantially flat disc 20 as shown in FIG. 2, in which the same reference numerals are used to indicate similar parts.

To prevent the femoral component rotating on spigot 5, bore 3 and spigot 5 can be made slightly oval or the spigot can be provided with a flat facet 12 which is aligned with a similar flat facet 13 in the bore. In another alternative construction a groove or keyway indicated by broken lines 14 can be provided on the component with a co-operating key on the bone. In all arrangements however, these anti-rotation features extend lengthwise of bore 3 and no spiral features or circumferential grooves or ridges are permitted.

In order to locate the femoral component on the bone, the femoral head is first shaped to provide tapered spigot 5, and the inside of bore 3 or the surface of the spigot 5 is covered with suitable cement. Femoral component 1 is now pushed into the position shown in the drawing, the cement mantle and the taper acting to hold the component in place and the appropriate features preventing rotation.

The interface between the bone cement and the bone is protected against shear and damage and the interface between the walls of the bore 3 and the cement is such that should there be any creep in the cement or movement in the bone, this is taken up by the component moving further over spigot 5, the polished surface of bore 3 allowing this movement to take place and the taper enabling the parts to lock together again.

Spacer 8 prevents cement from entering the void 9 so that there is space within the bore for the spigot to move further inwardly, spacer 8 moving with the spigot. Thus, should any loosening tend to occur, the assembly will relock.

Figure 3:
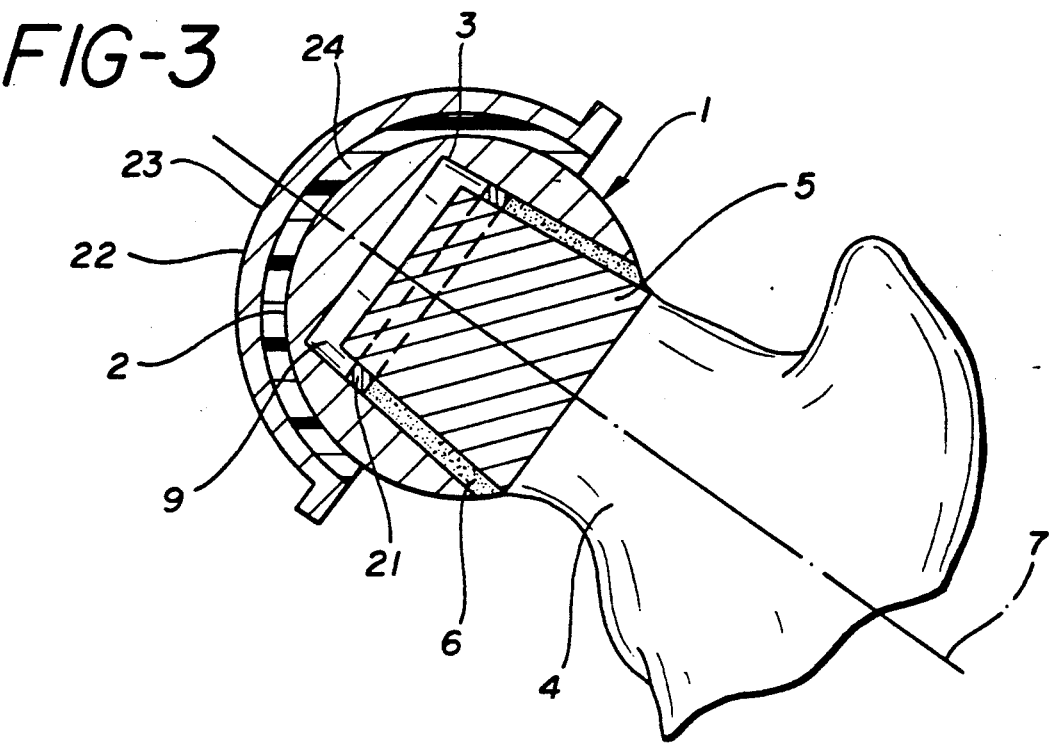
FIGS. 3, 4, 5 and 6 are similar views of further constructions.

In an alternative arrangement as shown in FIG. 3, the spacer 8 is provided merely as a collar of, for example, polymethylmethacrylate, and which will be slipped over the distal end of the spigot. The collar acts as a seal to prevent cement from entering the portion of bore 3 beyond the distal end of the spigot, thus creating the necessary void. With this arrangement, however, it is necessary for the surgeon to apply the cement only to the surface of the spigot distally of the collar so that when the component is pushed into place cement cannot enter the void created in bore 3. FIG. 3 also shows an acetabular socket 22 comprising an outer shell 23 and a bearing liner 24, which can be used with the replacement femoral component of the invention, makes up a total prosthesis.

Figure 4:
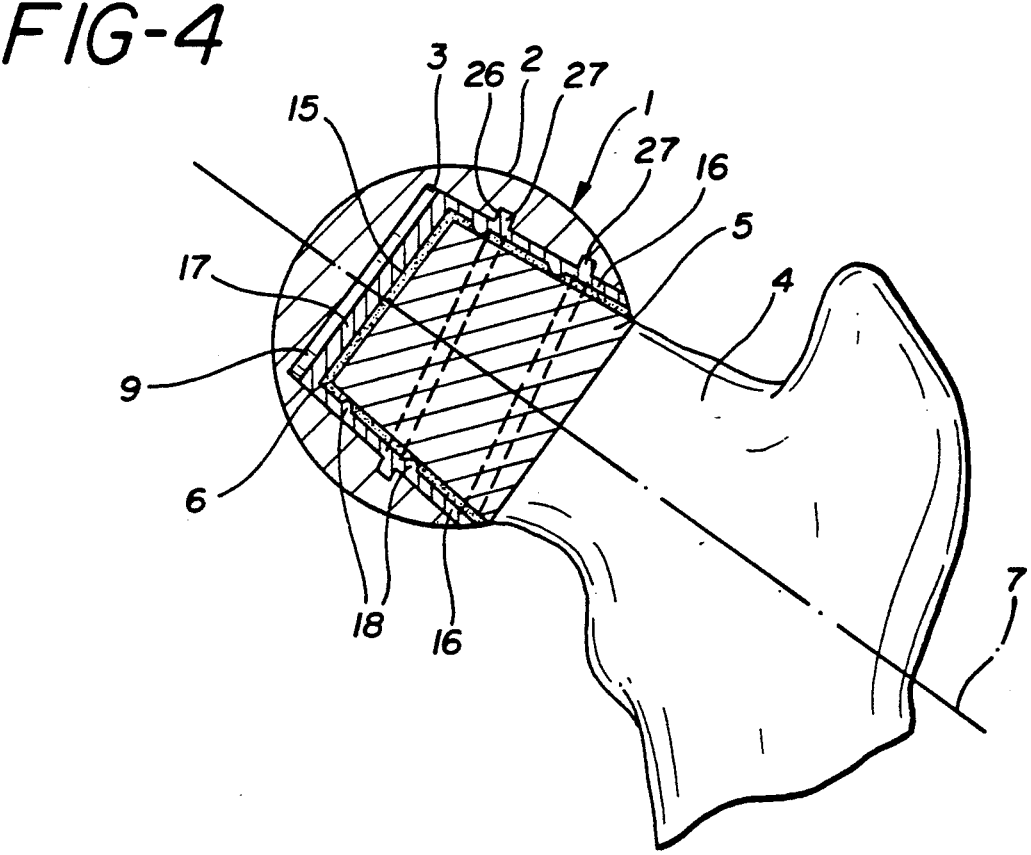

Another embodiment according to the present invention is shown in FIG. 4 wherein the same reference numerals are used to indicated similar parts. In this embodiment, however, a spacer 15 is provided which is generally cup-shaped and has side walls 16 which extend from a bore 17 outwardly for the full length of the bore 3. The side walls are a close fit in the bore 3. Spacer 15 is again made from polymethylmethacrylate so that it is fully compatible with the bone cement which is used and, in fact, provides what is in effect a preformed cement mantle. Spacer 15 and its side walls are made prior to fitting within bore 3 and is not molded within the bore. Thus, it can move within the bore to absorb relative movement between the bone and the femoral component.

If desired, protuberances can be formed integral with the preformed spacer and these act to locate spigot 5 when it is inserted. Bone cement 6 acts to secure spigot 5 to the mantel provided by the spacer and becomes effectively integral with it. Thus, any relative movement between the parts tends to be absorbed by movement of the preformed cement mantle provided by the spacer creator and the inner wall of the bore 3.

FIG. 4 also shows a construction in which the femoral component can rotate slightly rather than having the anti-rotation features described with regard to FIG. 1. Thus, the inner surface of the bore 3 is provided with a spiral groove 26 and the outer surface of the side wall 16 of the void creator 15 are provided with a spiral ridge to cooperate with the groove. Any inward movement of the bone and the void creator into the bore 3 of the femoral component therefore creates a slight relative rotation.

Figure 5:
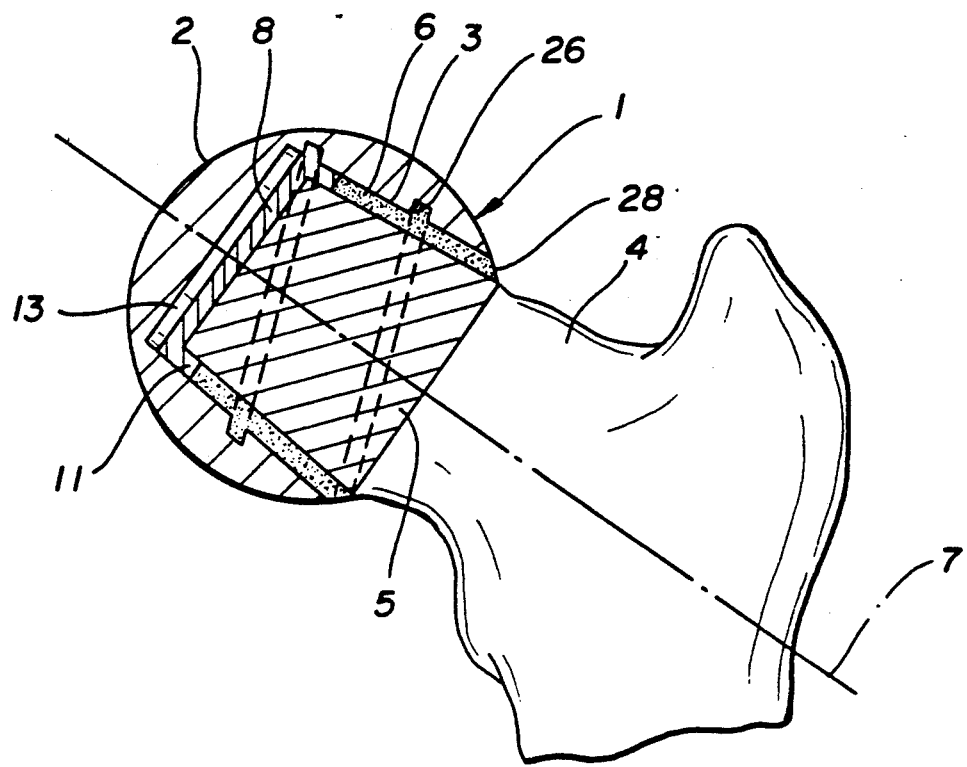

If it is desired to allow this type of rotation between the femoral component and the bone then the anti-rotation means shown in FIG. 1 can be replaced appropriately in any of the constructions shown;

FIG. 5 shows another construction in which relative rotation is again allowed, but in this case the configuration of the spacer void creator is similar to that shown in FIG. 1, that is the side walls do not extend throughout the length of the bore 3 of the component. As will be seen from FIG. 5, the spiral groove 26 is again provided but with this arrangement the groove is filled by the cement 6 which, when it has set, provides what is in effect ridges extending into the grooves 26 so that the movement is created.

Figure 6:
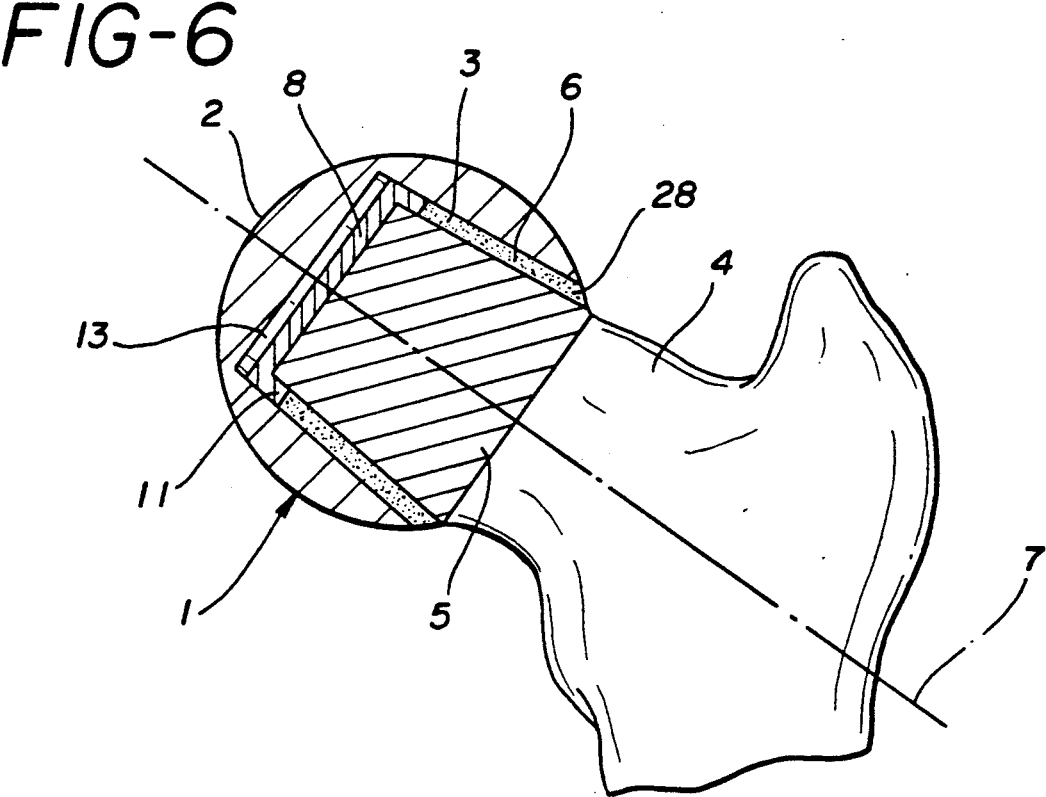

FIG. 5 also shows a construction in which the wall of the internal bore, although being inwardly tapered, is not parallel with the wall of the tapered spigot 5. It will be seen that the angle of the wall of the bore 3 is less than the angle of the wall of the spigot 5 so that the thickness of the cement 6 at the outer end 28 of the bore 3 is thicker than at the inner end; and FIG. 6 shows another construction in which the taper angles are dissimilar and which are arranged so that the thickness of the cement mantle is shallower at the open end 28 than at the inner end. Such an arrangement can also be achieved by making the internal bore 3 of parabolic form. Such constructions can again be provided with anti-rotation features or with rotation features as desired.

The invention also includes a total hip prosthesis incorporating a femoral component as described above. Thus, the total assembly could provide an artificial hip acetabular cup together with the femoral component of the kind set forth above.

While several examples of the present invention have been described, it is obvious that many changes and modifications may be made thereunto, without departing from the spirit and scope of the invention.

We claim:

1. A femoral prosthesis adapted to be cemented to a prepared natural femoral head, the prepared head having a conically tapered outer surface, comprising:
   a ball-shaped component having an outer surface conforming to an acetabular socket, said ball-shaped outer component having a blind bore formed therein, said bore tapering inwardly from a larger diameter at an open distal end thereof to a smaller diameter at the blind end of the bore, said taper generally matching the taper of the prepared head; and
   a deformable spacer for insertion into said bore having an outer diameter larger than said smaller diameter at the blind end of said bore, and smaller than said larger diameter at the open end of said bore, whereby said spacer prevents admission of bone cement into said bore and creates a void at the blind end of said bore after insertion therein and cementation of said ball-shaped component to the prepared natural femoral head.

2. The femoral prosthesis as set forth in claim 1 wherein said spacer is made of polymethylmethacrylate.

3. The femoral prosthesis as set forth in claim 1 wherein said spacer is cup-shaped with side walls extending to the distal end of said bore after insertion therein.

4. The femoral prosthesis of claim 1 wherein said ball-shaped component includes a means for preventing rotation thereof around the prepared natural femoral head.

5. The femoral prosthesis as set forth in claim 4 wherein the natural femoral head is prepared with a raised key and said means for preventing rotation is a keyway formed in said bore of said ball-shaped component.

6. The femoral prosthesis as set forth in claim 4 wherein the natural femoral head is prepared with a flat face and said means for preventing rotation is a corresponding flat face formed on said bore of said ball-shaped component.

7. A prosthetic femoral component for implantation on a conically tapered prepared end of a natural femur with bone cement, comprising:
   a deformable spacer having a disc-shaped base and a conical wall extending from said base and having an inner and outer surface tapering inwardly toward said base from a larger diameter of said spacer at an open end thereof, said conical walls of said spacer defining an opening for receiving the conically tapered prepared end of a natural femur; and
   a ball-shaped component having a blind bore formed therein, said bore tapering inwardly from a larger diameter at an open end thereof to a smaller diameter at the blind end thereof, said open end of said bore having a diameter large enough to receive said spacer therein and having a taper generally corresponding to said taper of said conical wall of said spacer, wherein said spacer prevents admission of bone cement into said bore and creates a void at the blind end of said bore after insertion therein and cementation of said ball-shaped component to the prepared natural femoral head.

8. The femoral prosthesis as set forth in claim 7 wherein said spacer is made of polymethylmethacrylate.

9. The femoral prosthesis of claim 7 wherein said ball-shaped component includes a means for preventing rotation thereof around the prepared natural femoral head.

10. The femoral prosthesis as set forth in claim 7 wherein the natural femoral head is prepared with a flat face, and said means for preventing rotation is a corresponding flat face form on said bore of said ball-shaped component.

* * * * *